(12) United States Patent
Dieckmann et al.

(10) Patent No.: US 6,201,053 B1
(45) Date of Patent: *Mar. 13, 2001

(54) PARTIALLY SAPONIFIED TRIGLYCERIDES, THEIR METHODS OF MANUFACTURE AND USE AS POLYMER ADDITIVES

(75) Inventors: Dale J. Dieckmann, Olathe; Wayne H. Nyberg, Overland Park, both of KS (US)

(73) Assignee: American Ingredients Company, Kansas City, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/574,808

(22) Filed: May 19, 2000

Related U.S. Application Data

(63) Continuation of application No. 09/538,840, filed on Mar. 30, 2000, which is a continuation of application No. 09/126,805, filed on Jul. 31, 1998, now Pat. No. 6,127,326.

(51) Int. Cl.$^7$ .............................. C08K 5/10; C08L 91/00; C10L 129/26; C10L 129/74
(52) U.S. Cl. ..................... 524/301; 524/306; 524/310; 524/312; 524/313; 508/491; 508/493
(58) Field of Search .................................. 524/301, 306, 524/310, 312, 313; 508/491, 493

(56) References Cited

U.S. PATENT DOCUMENTS

| 000,001 | 7/1790 | Hopkins ................................. 295/4 |
| 4,141,866 | 2/1979 | Foulks, Jr. ...................... 260/23 XA |
| 4,283,310 | * 8/1981 | James et al. ......................... 524/278 |
| 4,283,315 | * 8/1981 | James et al. ......................... 524/174 |
| 4,824,583 | 4/1989 | Hyde ..................................... 252/39 |
| 5,300,242 | 4/1994 | Nichols, et al. ...................... 252/38 |

FOREIGN PATENT DOCUMENTS

| 0 071 987 | 2/1983 | (EP) . |
| 944519 | 4/1949 | (FR) . |
| 944520 | 4/1949 | (FR) . |
| 315813 | 7/1929 | (GB) . |
| 964577 | 7/1964 | (GB) . |
| 1 375 289 | 11/1974 | (GB) . |
| 1 497 285 | 1/1978 | (GB) . |

OTHER PUBLICATIONS

Dieckmann, et al., *Lactic Acid Derivatives as Neutralizers in Polypropylene*, "Polyolefins VIII", SPE Regional Technical Conference, Feb. 22–24, 1993, Houston, Texas.

Rabinovitch, et al, *The Lubrication Mechanism of Calcium Stearate/Paraffin Wax Systems in PVC Compounds*, ANTEC '84, pp. 848–851.

American Ingredients Company, Patco Polymer Additives Division, *Test Method Polymer Corrosivity*, Revised: May 1, 1997.

* cited by examiner

Primary Examiner—Margaret Medley
Assistant Examiner—Cephia D. Toomer
(74) Attorney, Agent, or Firm—Wood Herron & Evans, L.L.P.

(57) ABSTRACT

Homogeneous partially saponified triglycerides are made consisting essentially of metal salts or fatty acid and mono-, di- and tri-glycerides without the need for a compatibilizing additive. The PSTs are useful as lubricants, antistats, stabilizers, coupling agents, waterproofing agents and neutralizers for polymers. The PSTs are formed in situ by reacting a fat or oil under controlled conditions with a catalyst and at a sufficiently high temperature to achieve a homogeneous composition. The PSTs also have a variety of end-uses other than as polymer additives, for example, as external lubricants, coupling agents, viscosity controllers, thickening agents, surfactants and waterproofing agents.

23 Claims, No Drawings

PARTIALLY SAPONIFIED TRIGLYCERIDES, THEIR METHODS OF MANUFACTURE AND USE AS POLYMER ADDITIVES

RELATED APPLICATIONS

This application is a continuation-in-part of U.S. patent application Ser. No. 09/126,805, filed Jul. 31, 1998 now U.S. Pat. No. 6,127,326, and continuing U.S. patent application Ser. No. 09/538,840, filed Mar. 30, 2000.

BACKGROUND OF THE INVENTION

Triglycerides occur as normal constituents of all forms of animal, vegetable and marine life. The fats of sea life are characterized by the presence of high molecular weight, highly unsaturated acids associated with only minor amounts of saturated acids. In contrast, the fats of land animals contain large amounts of $C_{16}$ and $C_{18}$ saturated and unsaturated acids, whereas fats of vegetable origin contain substantial amounts of closely related acids which are characteristic of a particular source.

Our ancestors developed many specific uses for fats in addition to their use as foods. It is believed that saponification was the first chemical reaction to which oils and fats were subjected, and the early chemical history of these substances actually constitutes a study of this process. The products of saponification offered the initial clue to the actual structure of the fats. Soaps were first prepared by boiling fats with wood ashes and were considered to be a combination of the fats with the ash constituents. Later, caustic was substitued for the wood ashes. The first United States patent was issued in 1790 to Samuel Hopkins, as signed by George Washington, and it covered the making of pearl-ash as an ingredient of soap manufacture.

It is necessary to go far back into chemical history in order to retrace the various contributions which have culminated in our present ideas concerning fats and saponification. More recently, however, improvements in partial saponification of fats were made. For example, when mixtures of salts of fatty acids and esters of fatty acids are produced by partial saponification, there is a tendency of the salts (soaps) to separate into curds. U.S. Pat. No. 4,824,583 issued in 1989 and it concerns the problem of incompatibility of soaps and esters produced during partial saponification. In order to produce soaps and esters as a homogeneous composition, oxidized polyethylene was used during partial saponification. It was believed that the oxidized polyethylene, particularly the functional carboxyl groups, reacted with components of the saponification mixture to form esters which were believed to promote homogeneity of the composition. Furthermore, in this '583 patent, the partially saponified triglycerides resulting from the reaction with oxidized polyethylene were used as lubricants in rigid PVC compositions.

In brief, hydrolysis of triglycerides with alkaline or alkaline earth metal bases is ancient. The reaction produces glycerol and a mixture of metal salts when one hundred percent of the saponification of the starting triglyceride is achieved. When saponification is less than one hundred percent, mono-substituted and di-substituted glycerides are obtained with triglycerides. However, there has been very little activity as represented by the above '583 patent for the use of partial saponification products as polymer additives. This may be in part attributable to the evolution of the metallic stearate and glyceryl ester industries because both of these industries predate polymers and plastics industries. In the continuing search for more cost-effective solutions in non-polymer areas, high-purity stearate products evolved first. By the time polymer applications became commercial opportunities, additives manufacturers had production facilities dedicated to making high-purity products.

Against this background, this invention is directed to improvements in partially saponified triglycerides, their methods of manufacture, applications as polymer additives, and use in other areas.

SUMMARY OF THE INVENTION

This invention relates to homogeneous partially saponified triglycerides (PSTs) which consist essentially of a metal salt of a fatty acid (soap) and glycerides. The PST comprises the reaction product of a fat or oil with a metal base, where the metal base is present in an insufficient amount to completely convert the ester to a soap. The reaction product is a homogeneous composition of a soap and a mixture of monoglyceride, diglyceride, and triglyceride with a minor amount of glycerine. By "homogeneous", it is meant that the metal soap and glyceride components are uniformly dispersed in each other and behave as one phase.

It has been found under controlled reaction conditions that a homogeneous composition of partially saponified triglycerides is obtained in the absence of a compatibilizing agent such as has been found necessary in the prior art mentioned in the background of this invention.

According to the method of this invention, a triglyceride is reacted with a metal base in the presence of a catalyst. The metal base is selected from a class of metal oxides, hydroxides, and carbonates, preferably of the alkali metal and alkaline earth metal class, most preferably calcium or sodium hydroxide. The reaction may be conducted under anhydrous conditions, but it is preferred to react the components with a very minor amount of water on the order of about 0.1 to about 2 percent by weight. The use of a minor amount of water not only facilitates the reaction but eliminates the formation of the reaction products and offensive odors that occur under anhydrous conditions. A variety of catalysts may be employed but organic acids or their salts are especially preferred, particularly low molecular weight acids such as glacial acetic acid on the order of about 0.1 to about 2 percent by weight. It is necessary to conduct the reaction at a sufficiently high temperature for solubilization or homogenization of the metal salt in the glycerides reaction mixture. It has been found, for example, that reaction temperatures in excess of about 120° C., preferably about 150° C. to about 250° C., are necessary to achieve the solubilization of the fatty acid salt in the reaction mixture. By achieving this solubilization, homogeneous partially saponified triglycerides are obtained without the need for the addition of compatibilizing agents of the type set forth in the background of this invention. In other words, essentially pure homogeneous partially saponified triglycerides are achieved according to the methodology of this invention.

It has also been found that the homogeneous partially saponified triglycerides are very useful as polymer additives and in other areas. In particular, the homogeneous PSTs are suitable for use as lubricants in vinyl halide resin formulations, particularly PVC. The homogeneous PSTs also serve as antistats in PVC compositions. Polyolefin resins such as polypropylene and propylene-ethylene copolymers are neutralized against corrosive activity by the homogeneous PSTs.

SUMMARY OF BEST MODES OF PRACTICING THE INVENTION

The best modes of practice involve reaction of triglycerides with a small amount of an organic acid catalyst, water and a metal base to give a homogeneous composition of the respective soaps and mono-, di- and tri-glycerides. An important step in this preferred mode of reaction is to use an organic acid, such as glacial acetic acid or its salt, and a small amount of water. In order to achieve the homogeneity in the reaction product, it is important that after the fatty acids soaps start to come out of solution, that the soaps in the reaction mixture redissolve. There are a number of advantages associated with this method. For example, homogeneous PSTs are achieved as relatively thick liquids which can be pumped or completely emptied from the reaction vessel. It has been found that the homogeneous PSTs produced by this method avoid the need for compatibilizing agents such as oxidized polyethylene that heretofore has been found necessary in order to achieve homogeneity of the partially saponified triglycerides.

The catalysts are used in amounts of about 0.1 to about 2 parts by weight. A very minor amount of water is also preferably required, in the order of about 0.1 to about 2 percent by weight. While water may be eliminated, the total elimination causes objectionable odor, probably from the formation of polyglycerols and/or acrolein from the glycerine formed in the hydrolysis. While foam may develop because of the presence of water, a defoamer can be used to control it. The following is a summary of synthesis components and conditions.

Triglycerides

Any fat or oil may be employed as a triglyceride. Those triglycerides that have been found satisfactory include tallow, fully hydrogenated tallow, soybean oil, partially hydrogenated soybean oil, fully hydrogenated soybean oil, fully hydrogenated high erucic rapeseed oil, fully hydrogenated castor oil, fully hydrogenated palm oil, canola oil, coconut oil, fully hydrogenated coconut oil, sunflower oil, lard, partially hydrogenated lard and macadamia oil. The fully hydrogenated fats or oils are especially preferred because they may be more readily granulated or flaked into solids at ambient temperature.

Metal Bases

The alkali and alkaline earth metal bases that have been found especially suitable include calcium hydroxide, sodium hydroxide, potassium hydroxide, lithium hydroxide and mixtures of these bases. Metal oxides and carbonates are also suitable bases. At present, those bases that have not been found to provide satisfactory results include magnesium hydroxide, magnesium oxide, zinc hydroxide, zinc oxide, aluminum oxide, ammonium hydroxide and triethanolamine.

Catalysts

A variety of catalysts have been found to promote the reaction. Organic acids and their salts are acceptable including glacial acetic acid, formic acid, propionic acid, caproic acid, lactic acid, stearic acid, oleic acid, calcium acetate and calcium lactate. Diethanolamine, triethanolamine, and ammonium hydroxide are suitable. At present, catalysts that were not found acceptable include sulfuric acid, p-toluenesulfonic acid, octadecylamine, diethylamine, pyridine, erucamide, triphenyl phosphite, tris(nonylphenyl) phosphite, propylene glycol and ethyl acetate. The preferred catalyst is glacial acetic acid and has been employed in amounts of about 0.1 to about 2 percent by weight of reactants.

Temperatures and Stoichiometry of the Reaction

It has been found necessary to conduct the reaction at a sufficiently high temperature to obtain solubilization or homogenization of the salts in the reaction mixture in order to achieve homogeneous PSTs. Temperatures on the order of about 150° C. to about 250° C. have been found satisfactory. Temperatures on the order of about 120° C. tend to be too slow. Furthermore, at temperatures lower than 120° C. reactions did not occur to enable the necessary solubilization and homogeneity of the salts in the reaction product. The stoichiometry of the metal base and triglyceride reactants may be varied such that the metal base is present in an insufficient amount to completely convert the triglyceride to a soap. Stoichiometric ratios of 2:1, 1.5:1, 1:1, 1:1.5 of calcium hydroxide to triglyceride molar ratio all have yielded satisfactory products. In general, the homogeneous partially saponified triglycerides include about 5 to about 95 percent by weight metal soaps, preferably about 35% to about 75% by weight, with the balance being a glyceride mixture of about 95% to about 5% by weight of monoglyceride, diglyceride, and triglyceride, preferably about 25% to about 65% by weight, and a minor amount of glycerine. Typically, for example, a preparation for calcium PST from fully hydrogenated soybean oil has the composition of 61.5% calcium stearate, 8.5% glyceryl tristearate, 17% glyceryl distearate, 11.5% glyceryl monostearate and 1.5% glycerine.

PSTs as Polymer Additives

The PSTs of this invention have been found effective lubricants and antistats in vinyl halide resin compositions. Vinyl halide resins are exemplified by polyvinyl chloride (PVC), but other halogen-containing resins fall into this class as understood in the art. Furthermore, the PSTs may be employed as lubricants or dispersion aids in a broad class of polymers such as polyesters, polystyrenes, elastomers, phenolics, ABS polymers and many others. This broad class of polymers is divided into subclasses of thermoplastic polymers and thermosetting polymers which are more detailed hereinafter. Tests in polyolefins such as polypropylene and propylene-ethylene copolymers show neutralization of catalyst residues by PSTs. Compared with presently available calcium stearate, PSTs have many desirable properties including lower melting point for more end-use applications; lower melt viscosity to render them pumpable as a melt; lower melting point and viscosity to make them flakable; made from fat or oil, with less heat history and better color than available products; clear melting; competitive costs and very easy to make kosher.

The PSTs are employed as additives in the above described polymers which are thermoplastic polymers and thermosetting polymers. When employed as polymer additives in thermoplastic or thermosetting polymers, the PSTs are generally used in amounts up to about 10% by weight of the polymers, more normally in amounts of about 0.05 to about 5% by weight and, preferably, about 0.05 to about 2% by weight. The PSTs provide a number of different functions in the polymer composition, depending upon the desired end-use. They function as antistats, lubricants, neutralizers, coupling agents or stabilizers, and combinations of these functions. As more particularly described hereinafter, the amount of the PST in the polymer composition depends upon the desired end-use. For example, when employed as a stabilizer or lubricant in a thermoplastic polymer such as a vinyl chloride resin, the PST is used in an amount of from about 0.05 to about 2 parts per 100 parts (0.05 to 2% by weight) polymer. When the PST is employed as an antistat in a vinyl halide resin, it is contained in an amount of from about 500 to about 2500 ppm. In a polyolefin polymer composition, such as polyethylene or polypropylene, and copolymers thereof, the PSTs are contained as lubricants of neutralizers in amounts of from about 0.05 to about 2 percent by weight resin. These amounts may vary as one of ordinary skill in the art may understand in view of the detailed description hereinafter.

In addition to the use of PSTs as polymer additives, they can be of use in other areas, such as lubricants for particulate solids or powders, coupling agents, waterproofing agents, viscosity controllers, surfactants and thickeners for a wide variety of polymeric and nonpolymeric compositions, or other end-uses, as further described hereinafter.

These and other advantages of this invention may be understood with reference to the following detailed description.

DETAILED DESCRIPTION OF THE INVENTION

The following operating examples demonstrate the practice of the invention and its various embodiments for making the partially saponified triglycerides and using them as polymer additives. To facilitate this description, the following abbreviations and definitions are employed.

1-mono means the amount of glycerol monoester having its ester on the #1 or #3 carbons of the glycerine backbone. Most glycerol monoester ($\geq 95\%$) is 1-mono.

CMP means capillary melting point.

FFA means free fatty acid which is not part of a glyceryl ester or soap.

FG means free glycerine which is not part of a glyceryl ester.

FHCO means fully hydrogenated castor oil.

FHP means fully hydrogenated palm oil.

FHSO means fully hydrogenated soybean oil.

FHT means fully hydrogenated tallow.

FTIR means infrared trace.

HOAc means glacial acetic acid.

HPLC means high pressure liquid chromatography which represents an analysis of the glyceride fraction of the PST, preferably about 25% to about 65% of the product. HPLC reports relative % mono, di, and triester components and can also provide a rough estimate of the total glyceride content. The rest of the PST comprises a large amount of metallic soap, preferably about 35% to about 75%, and small amounts of FG and FFA.

M/D means mono/di.

m.p. means melting point.

PST means partially saponified triglycerides(s).

SBO means soy bean oil.

I. Preparation of Partially Saponified Triglycerides and Comparative Examples 1–86

The equipment set up for the following examples consisted of a 4-neck round bottom flask fitted with a stirring paddle, a Frederick condenser, a thermometer, a gas inlet tube, and a closed-tube dropping funnel. A heating mantle was used with a variable powerstat as the heating source and nitrogen gas was used as an inert gas to blanket the ingredients in the reaction flask.

EXAMPLE 1

In this example, 365 g (0.4 moles) FHSO, 29.6 g (0.4 moles) Ca(OH)$_2$, 5.0 ml HOAc, and 9 g H$_2$O were reacted. The procedure using these reagents involved adding the FHSO to the reaction flask followed by the Ca(OH)$_2$. The reaction was heated using the heating mantle and when the FHSO melted the stirrer was turned on and nitrogen gas was allowed to flow over the reaction mixture. Now the HOAc and water were added in one portion. As the temperature rose above 100° C. the water started condensing back into the reaction flask with a certain amount of noise. When the temperature reached 174° C. one could see a slight amount of foam in the flask. After one hour one can see solids coming out of solution. These solids are gooey in nature and the water continued condensing drop-wise from the condenser. The solids gradually went back into solution. After one and one-half hours the reaction was complete and the temperature did not exceed 174° C. The FTIR of this material shows a broad OH peak around 3300.2 cm$^{-1}$, an ester carbonyl peak around 1731 cm$^{-1}$ and the carbonyl peak of a metallic salt around 1556 cm$^{-1}$. The starting material shows no broad OH peak and no metallic salt peak on the FTIR. The analysis of this material gives 5.65% ash, CMP=112–114° C., FG=1.45%, 1-mono=12.28%, moisture=0.33%, FFA=0.04%. The HPLC indicated that the PST was approximately 42% glycerides.

EXAMPLE 2

Example 1 was repeated with the same reagents except canola 90 was used as the fat. The reaction time was one and one-half hours and there was a problem with foam in the flask. The FTIR showed a weak OH peak and a weak metallic carbonyl peak. However, if foaming were controlled, a satisfactory product would be produced.

EXAMPLE 3

Reagents used in this example were 365 g FHT, 29.63 g Ca(OH)$_2$, 5 ml HOAc, and 9 ml H$_2$O. This reaction was run for two hours and ten minutes and the temperature rose to 183° C. There was considerable foam in this reaction but it was controlled with faster stirring. It was observed that less water would probably yield less foam. The analysis on the PST gave 5.63% ash, FG=1.14%, 1-mono=10.8%, moisture=0.12%, FFA=0.42%, m.p.=103–113° C.

EXAMPLE 4

The objective of this example was to use sodium hydroxide instead of calcium hydroxide. 365 g of FHT, 16 g NaOH (0.4 moles), 5 ml HOAc, and 5.0 ml H$_2$O were used as reagents. The reaction time was two hours and twenty minutes and the temperature did not exceed 183° C. Considerable white solid was precipitated in the flask. This white material did not flow readily out of the flask after the reaction was over. A spatula was required to help get it out. The FTIR on this material had the right peaks. The analysis gave FG=1.01%, 1-mono=7.18%, moisture=0.68%, the m.p.=107–150° C.

EXAMPLE 5

In this example, 365 g FHT, 32 g (0.8 moles) NaOH, 5 ml HOAc, 5 ml H$_2$O were reacted. Time of the reaction was one hour and fifty-two minutes. The temperature did not exceed 178° C. and little foam was seen during the reaction. The FTIR's had the correct peaks for a PST.

EXAMPLE 6

The objective of this example was to make the zinc salt. 365 g FHT, 32.54 g ZnO (0.4 moles), 5 ml HOAc, and 5 g H$_2$O were used. This reaction was run for four and one-half hours at a temperature as high as 243° C.; and at the end of this time the FTIR showed a OH peak and a carbonyl peak of a salt, but not enough to indicate full reaction. In other words, a homogeneous PST was not obtained under these conditions.

EXAMPLE 7

The object of this example was to use different triglycerides and in this case fully hydrogenated high erucic rapeseed oil. The reagents used were 365 g fat, 29.63 g Ca(OH)$_2$, 5 ml HOAc, and 5 ml H$_2$O. The time of the reaction was one hour and forty minutes and the temperature did not exceed 183° C. Added all ingredients at the start and noticed drop-wise reflux when the temperature was 133° C. At a temperature of 158° C. some foaming occurred so the condenser was removed to evaporate some of the water. Solids formed in the reaction flask but gradually broke up and became gooey. The reaction mixture became clearer and was amber in color. Some fumes were noticed coming out of the condenser. After the mentioned time the reaction mixture was poured into an aluminum pan where it solidified. HPLC showed 41.15% di, 37.96% mono, and 20.89% triglyceride on the material that was soluble in the HPLC solution. Ash=4.11 %, m.p.=111–115° C., FFA=0.08%, glycerine=0.72%, and the odor was mild.

EXAMPLE 8

The object of this example was to use FHCO as the lipid. Reagents consisted of 365.0 g FHCO, 29.63 g Ca(OH)$_2$, 5 ml HOAc, and 4 ml water at 125° C. for 30 minutes. This combination of ingredients created lots of foam. This foam is not easily controlled and foams out the condenser. Tried twice with the same results.

EXAMPLE 9

FHP was used in this example and reagents included 365.0 g FHP, 29.63 g Ca(OH)$_2$, 5 ml HOAc, and 5 ml water. Reaction time was one and one-half hours and the temperature rose no higher than 180° C. After about forty-five minutes solids started coming out of the reaction mixture. Solids were sticky but were broken up and went into solution. The resulting mixture looked like honey. The FTIR looked good with the usual OH and carbonyl peaks.

EXAMPLE 10

In this example, 365 g coconut oil (92 deg-C T Quincy), 29.63 g Ca(OH)$_2$, 5 ml HOAc, and 5 ml water were reacted. Reaction time was two hours and forty-five minutes. The temperature rose to 250° C. and an attempt was made to dissolve a ball formation. This was an unacceptable reaction, believed attributable to the wrong weight for the oil.

EXAMPLE 11

Example 10 was repeated using 268 g of the oil. Reaction time was two hours and ten minutes and the temperature rose to 240° C. There were still a lot of undissolved solids in the reaction and this was not completely acceptable. More process work is required with coconut oil.

EXAMPLE 12

268 g fully hydrogenated coconut oil, 29.63 g Ca(OH)$_2$, 6 ml HOAc, and 6 ml water were reacted. The reaction ran for almost three hours and the temperature rose to 163° C. A big lump was formed which would not break up. This was not an acceptable run.

EXAMPLE 13

Example 12 was repeated but changed to only 5.1 ml HOAc and 2 g water. The reaction ran for about two hours. The temperature got up to 170° C. and after one hour a large ball was noticed in the flask, but this time the ball became gooey and broke up. The product of this reaction seemed very oily, but is acceptable.

EXAMPLE 14

FHSO 268 g (0.293 moles), Ca(OH)$_2$ 44.45 g (0.6 moles), 5 g HOAc and 2 g water were reacted. The reaction ran about one hour and fifteen minutes and the temperature did not get over 185° C. After about forty-five minutes considerable foam was noted and was controlled. There was no ester carbonyl in this product, just the carbonyl of the acid salts. The analysis showed m.p.=softens at 270° C., FFA=0.15%, FG=3.6%, Ca=7.82%.

EXAMPLE 15

268 g fully hydrogenated coconut oil (110 coconut) (0.4 moles), 29.63 g (0.4 moles) Ca(OH)$_2$, HOAc=5 g, and water 2 g were reacted. The reaction time was two hours and forty-five minutes and the high temperature was 178° C. Up to one inch of foam formed, and the solids that came out formed a large ball that looked gooey. This ball broke up and became one phase. The FTIR had peaks at 3300 cm$^{-1}$ for the OH, and 1743.75 cm$^{-1}$ for the ester carbonyl and 1550 cm$^{-1}$ for the acid salt.

EXAMPLE 16

365 g FHSO (0.4 moles), and 44.45 g Ca(OH)$_2$ (0.6 moles), 5 g HOAc, and 2 g water were reacted. The high temperature was 184° C. and after one hour and forty minutes, there was so much foam that it flowed out the condenser. This reaction was not acceptable, due to foaming.

EXAMPLE 17

365 g FHSO (0.4 moles), Ca(OH)$_2$ 29.63 g (0.4 moles), 5 g HOAc and 2 g water were reacted. The reaction time was one and one-half hours and the high temperature was 181° C. There was approximately one inch of foam and when the solids came out they were gooey but stirrable. This reaction was acceptable. The FTIR showed the correct carbonyl peaks for metal salt and ester carbonyl, as well as the OH peak.

EXAMPLE 18

396 g FHSO (0.45 moles), Ca(OH)$_2$ 22.2 g (0.3 moles), 5 g HOAc, and 2 g water were reacted at a ratio of 1.5:1. The reaction time was two hours and the temperature did not exceed 180° C. There was very little foam and the solids that came out went back into solution nicely and the reaction mixture poured out clear. The FTIR had the small OH peak, the ester carbonyl at 1731 cm$^{-1}$ and the metallic salt of the acids at 1550 cm$^{-1}$. The analysis gave 2.84% ash, 0.75% free glycerine, 1-mono of 8.83%, moisture of 0.32%, FFA of 1.08% and a m.p. of 111–115° C. clear melt. The HPLC showed 39.21 % di, 21.64% mono, and 39.15% triglyceride.

EXAMPLE 19

This example used a 1:1 ratio of FHSO 396 g (0.45 moles), Ca(OH)$_2$ 33.34 g (0.45 moles), 5 g (0.08 moles) HOAc, and 2 g water. This reaction went two hours and the temperature did not exceed 183° C. There was a foam problem and the foam went up the condenser. No analysis on this material was obtained.

EXAMPLE 20

Using the same amount of ingredients, Example 19 was repeated with the exception that 3.57 g HOAc and 1.43 g water were used. The reaction time was three hours and fifteen minutes and the high temperature was 189° C. After two hours a large ball formed in the flask so this reaction took longer for the solids to redissolve. No foam was observed, but perhaps either the longer time or reduced water caused the finished material to have an odor that was undesirable. Still, the right product was apparently made.

EXAMPLE 21

This example used FHSO 396 g (0.45 moles), Ca(OH)$_2$ 33.34 g (0.45 moles), 5 g HOAc, and 2 g water. The reaction time was two hours and the temperature did not exceed 182° C. After about one hour there seemed to be a good deal of foam in the reaction flask, so one drop of Patcote® 555 defoamer was added. This killed all the foam. As usual in the course of the reaction solids came out and redissolved. The final reaction material had no appreciable odor. The analysis showed 41.34% mono, 40.7% di, and 17.97% triglyceride. The ash was 7.8%, FG=1.53%, the 1-mono=12.39%, moisture=0.26%, FFA=0.99, m.p.=114–116° C. with clear melt.

EXAMPLE 22

In this example, an attempt was made to hydrolyze with water first then add the base after a certain period by reacting 396 g FHSO (0.45 moles), 5 g HOAc, and 2 g water followed after two hours by 33.34 g (0.45 moles) Ca(OH)$_2$. After the first two hours an FTIR was run and a peak appeared at 1637 cm$^{-1}$, which should be a free fatty acid peak, and the FTIR showed a huge OH peak because of the water in the reaction. After the first two hours 33.34 g (0.45 moles) Ca(OH)$_2$ was added, but before the addition of the base the condenser was removed to get rid of any excess water. The total reaction time was three hours and thirty minutes. There was no foam during the run and the solids that separated went back into solution nicely. After the reaction the mixture was poured into an aluminum pan and at that time it was noticed that it had an odor. It was also noted on the FTIR of the finished product that a peak appeared at around 1550 cm$^{-1}$.

EXAMPLE 23

The object of this example was to use a small amount of base to catalyze the formation of some mono/diglycerides which may act as a defoamer when all the soaps come out of solution. This reaction was run for three hours, using 396 g (0.45 moles) FHSO, 5 g HOAc, 2 g water, and 0.5 g Ca(OH)$_2$ which was added at the start of the reaction. The reaction temperature reached 176° C. for up to two hours when the 33 g Ca(OH)$_2$ was added. The reaction was now continued for up to three hours total, and the temperature got no higher than 180° C. This reaction had no foam and no odor. The HPLC analysis showed about 59% glycerides consisting of 41.84% di, 28.12% mono, and 30.04% triglyceride. The FG=0.79, the % ash=4.02%, the m.p.= 113–115° C. clear melt, and the moisture was 0.06%. The FTIR showed the correct peaks.

EXAMPLE 24

The object of this example was to use formic acid instead of glacial acetic acid to see if other acids would work by using 396 g (0.45 moles) FHSO, 0.5 g Ca(OH)$_2$ at the start, 5 g formic acid and 2 g water. After about two hours the 33 g of Ca(OH)$_2$ was added. The reaction was continued for another two and one-half hours and the temperature did not get over 200° C. There was no appreciable foam in this reaction but the solids that formed were loose and stirrable, but would not redissolve as other reactions have done. The FTIR of the solid showed an OH peak around 3400 cm$^{-1}$, a smaller ester carbonyl peak at 1737 cm$^{-1}$, and the salt peak at 1550 cm$^{-1}$. There was an extra peak around 1540 cm$^{-1}$. The main objection to this reaction was that the solids formed would not go back into solution. The product was not homogeneous under these conditions. More process work is required with formic acid catalyst.

EXAMPLE 25

The purpose of this example was to use calcium acetate instead of glacial acetic acid to see if the reaction would go using 396 g (0.45 moles) FHSO, 13 g calcium acetate, and 2 ml water. The reagents were reacted for two hours and the temperature did not exceed 170° C. An FTIR was taken after one hour which showed the ester carbonyl peak and no OH or metal salt peak. After two hours 30 g Ca(OH)$_2$ was added and the reaction continued for another hour and forty-five minutes. There was a small amount of foam and the solids came out and went back in as was seen in other good reactions. The FTIR of the final material showed a nice OH peak, an ester peak, and a doublet around 1540 cm$^{-1}$.

EXAMPLE 26

This example showed the effects of using calcium acetate and the other ingredients as described in Example 25, but all ingredients were added at the start of the reaction. This reaction went one hour and fifteen minutes and the temperature did not exceed 191° C. After one hour, foam developed and one drop of Patcote® 501K was added and the foam went down. The solids came out and went back into solution as expected. The FTIR showed the correct peaks.

EXAMPLE 27

This example was an attempt to make the M/D glyceride first, using 396 g (0.45 moles) FHSO, 13 g CaAc, 0.5 g Ca(OH)$_2$, and 2 ml water to start the reaction. During the first hour the temperature got up to 187° C. An FTIR was taken after this hour and no OH peak or metal salt carbonyl peak was observed. 30 g Ca(OH)$_2$ was then added. A small amount of foam developed but was not a problem. After two hours and forty-five minutes during which the flask contents were heated up to 190° C., a phase separation of solids occurred and gradually redissolved. An FTIR of the final product showed a nice OH peak, and ester peak, and a peak for the metal salt of an acid.

EXAMPLE 28

The object of this example was to omit the glacial acetic acid at the start of the reaction and then take an FTIR to see the effect, using 396 g (0.45 moles) FHSO, 33.34 g (0.45 moles) Ca(OH)$_2$, and 2 g water. The reaction ran for four hours and the temperature during this time got no higher than 190° C. An FTIR was taken after two hours to look for the characteristic peaks, but they were not there, only the ester peak at 1737.5 cm$^{-1}$ and a small peak at 3637.5 cm$^{-1}$ probably due to the Ca(OH)$_2$. At this time 5 g of glacial acetic acid were added and the reaction continued for another hour and twelve minutes. Drop-wise reflux was noticed and solids came out of solution after about one hour. These solids were stringy and gooey and eventually went into solution as seen in other reactions. An FTIR of the final material showed a nice OH peak at 3356.25 cm$^{-1}$, an ester peak at 1737.5 cm$^{-1}$, and the metal salt peak at 1543.75 cm$^{-1}$. This example demonstrates that a catalyst is needed to run this reaction.

EXAMPLE 29

This example was to test whether other organic acids would work using 396 g (0.45 moles) FHSO, 33.34 g (0.45 moles) Ca(OH)$_2$, 5 g propionic acid, and 2 g water. The reaction time was one hour and eleven minutes and the temperature did not exceed 195° C. After forty-five minutes a lot of solids came out along with considerable foam. One drop of Patcote® 501K broke the foam. The reaction product looked clear and the FTIR showed a nice OH peak at 3331.25 cm$^{-1}$, an ester peak at 1737.5 cm$^{-1}$, and the metal salt peak at 1543.75 cm$^{-1}$.

EXAMPLE 30

This example was set up to use stearic acid catalyst using 396 g (0.45 moles) FHSO, 23.7 g (0.08 moles) stearic acid, 33.34 g (0.45 moles) Ca(OH)$_2$, and 2 g water. After the reaction had been going for about one-half hour a lot of solids came out of solution. A total of 12 drops of Patcote® 501K was used to control the foam. An FTIR showed the correct peaks but foaming is a problem.

EXAMPLE 31

The objective of this example was to use capric acid as the acid ingredient, using 396 g (0.45 moles) FHSO, 33.3 g (0.45 moles) Ca(OH)$_2$, 2 g water, and 14.35 g (0.083 moles) capric acid. The reaction time was around one hour and forty minutes and the temperature did not rise above 187° C. After about thirty minutes there was sufficient foam so 1 drop of Patcote® 501K was added which controlled the foam nicely. The solids came out as usual and went back into solution. The final reaction mixture seemed clear. This was a good reaction except for moderate foam.

EXAMPLE 32

This example was run to test H$_2$SO$_4$ to see if the reaction would go using 396 g (0.45 moles) FHSO, 33.3 g (0.45 moles) Ca(OH)$_2$, 2 g water, and up to 20 g H$_2$SO$_4$. The reaction was run over a two hour period and the temperature did not get over 192° C. After one hour and fifty-two minutes an FTIR was run and it showed no reaction. The reaction was started with 2 drops of acid and toward the end up to 20 g acid was added. When the 20 g were added an uncontrollable amount of foam was produced. This was not an acceptable reaction.

EXAMPLE 33

Lactic acid was used in this example to see its effect, using 396 g (0.45 moles) FHSO, 33.3 g (0.45 moles) Ca(OH)$_2$, 1.5 g water, and 5.7 g lactic acid. This reaction went for two hours and forty-two minutes and the temperature rose to 182° C. After one hour one drop of Patcote® 501K was added to control foam. This reaction seemed to go and the finished material seemed to have an off-white color.

EXAMPLE 34

This example is the start of a new series of reactions where the amount of water was kept to a minimum and attempts were made not to use any defoamer, using 365 g (0.45 moles) FHSO, 44.45 g Ca(OH)$_2$ (0.6 moles), 2 g water, and 5 g HOAC. The ratio of reactants was 1 to 1.5. This reaction was run over a two hour period and the temperature did not rise above 194° C. After about a half-hour, solids started coming out and the foam rose to about one inch. No defoamer was used in this reaction. It was noted that when cool this product ground easily. The FTIR looked good with the characteristic peaks and the characteristic ester peak was much smaller. The HPLC analysis showed that only about 5 micrograms were recovered out of 22.5, indicating that there probably was a smaller amount of glyceride formed. The ash=5.9%, FG=5.11%, 1-mono=12.7%, moisture=0.66%, FFA=0.75%, m.p.=116–124° C. clear melt and the odor was moderate.

EXAMPLE 35

The ratio of reactants in this example was 1:1 using FHT 345 g (0.4 moles), Ca(OH)$_2$ 29.63 g (0.4 moles), 2 g water, and 5 g HOAc. The reaction was run for two hours and the temperature did not rise above 183° C. After about forty-five minutes there were large lumps and foam in the flask. One drop of Patcote® 501K defoamer was added. After about one hour the foam was down and the stirring was good. The solids went back into solution as usual. The FTIR looked good with the characteristic peaks and other analysis showed 4.03% ash, FG=2.5%, 1-mono=13.59%, moisture=0.55%, FFA=2.87%, the m.p.=105–110° C. clear melt, and the odor was mild.

EXAMPLE 36

Fully hydrogenated palm oil 322.7 g (0.4 moles), Ca(OH)$_2$ 29.63 g (0.4 moles), 5 g HOAc, and 2 g water were reacted. The reaction went for two hours and the temperature did not rise above 188° C. There seemed to be a considerable amount of foam in this reaction and four drops of Patcote® 501K had to be used. Other than the foaming, this reaction went satisfactorily. The FTIR showed the characteristic peaks.

EXAMPLE 37

Since the reaction in Example 26 seemed to have considerable foam it was decided to change the conditions to help lower the foam by using 322.73 g (0.4 moles) FHP, 29.63 g (0.4 moles) Ca(OH)$_2$, 5 g HOAc, and cutting the water to 0.5 ml. This reaction went for two hours and the temperature did not rise above 182° C. After about twenty minutes sufficient foam developed and one drop of Patcote® 501K defoamer was used. The FTIR showed the usual peaks, the OH peak at 3300 cm$^{-1}$, the ester carbonyl at 1750 cm$^{-1}$, and the metallic salt peak at 1543.75 cm$^{-1}$.

EXAMPLE 38

This example was a repeat of Example 37, except only one gram of water was used. The reaction time was two hours and the temperature did not go over 183° C. Again, this reaction required one drop of defoamer. The FTIR looked good as above.

EXAMPLE 39

Example 37 was again repeated only this time with 0.5 g of water. The reaction went for two hours and the temperature did not rise above 182° C. The amount of foam rose to one inch but was controlled. Sometimes the foam in this reaction could be controlled by speeding up the stirrer. The 0.5 g water used is probably the minimum for this reaction. The analysis showed FG=2.49%, FFA=1.89%, %Ca=4.5%, m.p.=105–108° C., moisture=0.55%, 1-mono=14.35% and the odor was moderate. The HPLC showed of the material recovered 44.54% di, 33.85% mono, and 21.62% triglyceride. The FTIR showed the correct OH and carbonyl absorptions.

EXAMPLE 40

This example is a continuation of using 0.5 g water with 396 g (0.45 moles) FHSO, 33.34 g (0.45 moles) Ca(OH)$_2$, and 5 g HOAc. This reaction went for one hour and twenty minutes and no defoamer was used. The analysis showed 1-mono=13.4%, FG=2.25%, ash=5.15%, m.p.=108–111° C. clear melt, moisture=0.52%, FFA=1.08% and the odor was mild. The FTIR showed characteristic important peaks at 3318.75 cm$^{-1}$, 1737.5 cm$^{-1}$ and 1543.75 cm$^{-1}$.

EXAMPLE 41

The ratio of reactants in this example was 1:1 using FHT 345 g (0.4 moles), 29.63 g Ca(OH)$_2$, 5 g HOAc, and 0.5 g water. This reaction went for one hour and the temperature did not rise over 180° C. No defoamer was used. The FTIR looked acceptable, the HPLC of the recovered material showed 39.38% di, 43.82% mono, and 16.8% triglyceride. The 1-mono=14.18%, FG=2.27%, ash 4.18%, m.p.= 106–109° C., moisture=0.54%, FFA=0.07, and the odor was moderate.

EXAMPLE 42

The ratio of reactants in this example was changed to 1:1.5, using 365 g FHSO (0.4 moles), 44.45 g (0.6 moles) Ca(OH)$_2$, 5 g HOAc and 0.5 g water. The reaction time was one hour and seven minutes and the temperature did not exceed 185° C. When the solids started coming out more foam developed and one drop Patcote® 501K had to be used. The FTIR had the characteristic peaks and it was noted that the ester carbonyl peak was much lower than usual probably since more base was used. The analysis showed 1-mono=15.65%, FG=4.98%, ash=5.86%, no m.p. recorded, moisture=0.93%, FFA=0.06%, and the odor was mild.

EXAMPLE 43

Fully hydrogenated high erucic rapeseed oil 292.69 g (0.3 moles), Ca(OH)$_2$ 22.22 g (0.3 moles), HOAc 3.75 g and 0.5 g water were used in this example. This reaction was run for one hour and five minutes and the temperature did not exceed 173° C. Some foam developed but was controlled. The FTIR looked acceptable and the HPLC had some extra peaks for which there were no references. The wet analysis showed 1-mono=12.37%, FG=1.97%, ash-3.73%, m.p.= 110–112° C. clear melt. Moisture=0.62%, FFA=0.12% and the odor was mild.

EXAMPLE 44

The ratio of reactants in this example was changed to 1.5:1, using 365 g FHSO (0.4 moles), Ca(OH)$_2$ 19.75 g (0.26 moles), 5 g HOAc, and 0.5 g water. The reaction time was one hour and the temperature did not exceed 173° C. No defoamer was used here and the finished reaction poured out clear. The FTIR looked good with the ester peak higher than the metallic carbonyl peak. The HPLC showed on the recovered material, 32.15% di, 18.39% mono, and 49.46% triglyceride. Other analysis showed 1-mono=8.83%, FG=0.9%, ash=2.73%, m.p.=111–115° C. clear melt, moisture=0.09%, FFA=0.24% and the odor was mild.

EXAMPLE 45

In this example, KOH was used as the base by reacting 365 g (0.4 moles) FHSO, 44.8 g (0.8 moles) KOH, 5 g HOAc, and 0.5 g water. The reaction time was one hour and twenty minutes and the temperature did not exceed 181° C. Some foam developed but it was controlled. This reaction mixture got thick like jelly. The FTIR had the correct peaks but the ester peak was much lower than the metallic carbonyl peak. The yield on this reaction was only 1.56 g less than the weight at the start. The HPLC recovered material showed 3.984% di, 3.18% mono, and 92.8% triglyceride. Other analysis showed 1-mono=0.1 %, FG=4.7%, m.p.=softened but never melted, moisture=1.86%, FFA=none detected, and the odor was moderate.

EXAMPLE 46

This example used NaOH as the base by reacting 365 g (0.4 moles) FHSO, 32 g (0.8 moles) NaOH, 5 g HOAc (glacial), and 0.5 g water. The reaction time was one and one-half hour and the temperature did not exceed 198° C. Some foam developed but was manageable. This reaction became thick and did not pour readily out of the reaction flask. The material after cooling did grind well. The FTIR showed the correct peaks and the HPLC on the recovered material showed 29.57% di, 20.98% mono, and 49.45% triglyceride. Other analysis showed 1-mono=7.14%, FG=1.51%, m.p.=softened@ 110° C. and was not completely melted at 200° C., FFA=none detected, and the odor was mild.

EXAMPLE 47

Canola oil was used as the lipid in this example in an amount of 354.4 g (0.4 moles), with Ca(OH)$_2$ 29.63 g (0.4 moles), 5 g HOAc, and 0.5 g water. The reaction time was one hour and eleven minutes and the temperature did not exceed 181° C. After about thirty-five minutes foam seemed excessive so one drop of Patcote® 501K was used. The solids came out of solution and then redissolved as usual. This reaction mixture was easily poured into an aluminum pan. On cooling the material was semi-solid and sticky. The FTIR showed an OH peak at 3262.5 cm$^{-1}$, an ester carbonyl at 1743 cm$^{-1}$, and a metallic salt peak at 1550 cm$^{-1}$. The HPLC of the dissolved material showed 35.98% di, 35.31 % mono, and 28.7% triglyceride. Other analysis gave 1-mono= 14.25%, FG=2.35%, ash=4.11%, m.p.=softened at 25 and completely melted at 80° C., FFA=1.63%, and the odor was mild.

EXAMPLE 48

353.6 g (0.4 moles) soybean oil, 29.63 g (0.4 moles) Ca(OH)$_2$, 5 g HOAc, and 0.5 g water were reacted. The reaction time was one hour and the temperature did not exceed 191° C. After about one-half hour some foam developed but was controllable. The FTIR of this material showed the correct peaks. The physical form was an amber sticky solid. The HPLC of the soluble material showed 37.8% di, 36.37% mono, and 25.83% triglyceride. Other analysis showed 1-mono=14.75%, FG=2.15%, ash=4.11%, m.p.= softens at room temperature and melts clear at 80° C., moisture=0.44%, FFA=1.28%, and the odor was mild.

EXAMPLE 49

In this example the base was changed to LiOH of which 34.25 g (0.8 moles) was used. Other reagents included FHSO at 365 g (0.4 moles), 5 g glacial acetic acid, and 0.5 g water. The reaction time was about one hour and forty-one minutes and the reaction temperature did not exceed 193° C. The LIOH used is a hydrated material so during the reaction a Dean Stark trap was used to collect a total of 10 ml of water. Some foam was generated but was controlled. At the end of the reaction the flask was full of white solid. The FTIR on this material showed a nice OH peak at 3550 cm$^{-1}$, an ester carbonyl peak at 1743/75 cm$^{-1}$, and a split metallic salt peak at 1581.25 cm$^{-1}$. The HPLC of the material soluble in the HPLC solution gave 44.53% di, 33.29% mono, and 22.18% triglyceride. Other analysis gave 12.27% 1-mono glyceride, FG=2.07%, m.p.=softened at 115 and up to 200° C. did not melt, moisture=0.54%, FFA=0.06%, and the odor was mild.

EXAMPLE 50

This example was an attempt to use MgO (Magox Super Premium) as the base, using 16.3 g (0.4 moles) MgO, 365 g (0.4 moles) FHSO, 5 g glacial acetic acid, and 0.5 g water. This reaction was run over a three-hour period and the temperature did not exceed 200° C. After about one hour an FTIR was run to see what the reaction was doing and at this point the characteristic peaks of the PSTs were not there. The reaction was then continued for a total time of three hours and again an FTIR was run. This FTIR showed no OH peak, an ester peak at 1737.5 cm$^{-1}$ and no metallic carbonyl peak. Based on these results no reaction occurred.

EXAMPLE 51

In this example, vegetable shortening (partially hydrolyzed soy) was used. The ratio of reactants was 1:1 with 365 g (0.4 moles) vegetable shortening, 29.64 g (0.4 moles) Ca(OH)$_2$, 5 g glacial acetic acid, and 0.5 g water. The reaction time was one hour and the temperature did not exceed 190° C. A small amount of foam was produced but it was not a problem. The reaction mixture poured out clear. The FTIR showed a broad OH peak around 3343 cm$^{-1}$, an ester peak at 1750 cm$^{-1}$, and a metallic acid carbonyl peak at 1537.5 cm$^{-1}$. The HPLC of the soluble material showed 39.69% di, 36.90% mono, and 23.41% triglyceride. Other analysis showed 1-mono=14.2%, FG=1.94%, ash=4.01%, m.p.=softened at 25° C. and completely clear at 70° C., moisture=0.34%, FFA=1.21%, and the odor was moderate.

EXAMPLE 52

In this example, a mixture of bases was used by reacting 14.8 g (0.2 moles) Ca(OH)$_2$, 16.0 g (0.4 moles) NaOH, 365 g (0.4 moles) FHSO, 5 g of glacial acetic acid and 0.5 g water. The NaOH was finely ground to help it disperse readily. The reaction time was one hour and eleven minutes and the temperature did not exceed 178° C. About two and one half inches of foam developed; however, it was controlled. The reaction at the end poured out clear into an aluminum pan. The FTIR had a broad OH peak around 3325 cm$^{-1}$, a smaller ester carbonyl peak at 1737.5 cm$^{-1}$, and the metallic salt of an acid peak at 1556.25 cm$^{-1}$. The HPLC of the material soluble in the sample solvent showed 46.75% di, 32.2% mono, and 21.06% triglyceride. Other analysis gave 1-mono=15.04%, FG=2.16%, ash=7.88%, m.p.=started to melt at 115° C. to 119° C. with a clear melt, moisture=0.34%, FFA=1.18%, and the odor was mild.

EXAMPLE 53

This example employed another variation in the lipid source by reacting 342 g (0.4 moles) sunflower oil, 29.63 g (0.4 moles) Ca(OH)$_2$, 5 g HOAc, and 0.5 g water. The reaction time was one hour and five minutes and the temperature did not rise above 182° C. There was considerable foam that developed and two drops of Patcote® 501K had to be used. The resulting product of this reaction was a thick sticky semi solid. The FTIR showed a broad OH peak around 3300 cm$^{-1}$, an ester carbonyl peak at 1743.28 cm$^{-1}$ and a metallic acid carbonyl peak at 1548.51 cm$^{-1}$. Other analysis showed 1-mono=16.51%, FG=2.67%, ash=3.80%, m.p.=softened at 25° C. and melted clear at 60° C., moisture=0.50%, FFA=1.57%, and the odor was mild.

EXAMPLE 54

Fully hydrogenated coconut oil was used in this example in an amount of 268 g (0.4 moles), with 29.63 g (0.4 moles) Ca(OH)$_2$, 5 g glacial acetic acid, and 0.5 g water. The reaction time was one hour and the temperature did not exceed 184° C. After about one-half hour considerable foam developed and one drop of Patcote® 501K was used. Other than some foam this reaction was satisfactory. The FTIR showed a broad OH absorption at 3350 cm$^{-1}$, an ester carbonyl peak at 1737.5 cm$^{-1}$ and a doublet for the metallic carbonyl at 1575 and 1556 cm$^{-1}$. The HPLC of this material was inconclusive because peaks developed for which there were no standards. Other analysis included 1-mono=17.15%, FG=3.10%, ash=5.14%, m.p.=softens at 25 and clear melt at 82° C., moisture—0.81%, FFA—3.41% and the odor was very mild.

EXAMPLE 55

Fully hydrogenated castor oil 287.5 g (0.3 moles), 22.22 g (0.3 moles) CaOH$_2$, 3.25 g HOAc, and 0.5 g water were reacted in this example. The reaction time was about one hour and the temperature did not exceed 188° C. Five drops of Patcote® 501K was used to control the foam. The FTIR of the final product showed a high broad OH peak at 3318.75 cm$^{-1}$, a medium ester carbonyl peak at 1737.5 cm$^{-1}$ and a metallic acid carbonyl peak at 1581.25 cm$^{-1}$. Other analysis gave 1-mono=20.04%, FG=1.91%, ash=4.37%, m.p.=137–141° C. clear melt, moisture=0.30%, FFA=0.95% and the odor was moderate.

EXAMPLE 56

This example was an attempt to use zinc hydroxide as the base by reacting 39.75 g (0.4 moles) Aldrich zinc hydroxide, 365 g (0.4 moles) FHSO, 5 g HOAc and 0.5 g water. The reaction time was a little over six hours, and the reaction temperature did not rise above 207° C. After one hour an FTIR was run and showed no reaction, at two hours an FTIR was run and there seemed to be a small amount of metallic acid carbonyl peak formed. At the end of the reaction there was, on the FTIR, a very small broad OH peak, a large ester carbonyl peak, and a small to medium peak in the region for the metallic acid carbonyl group. It is estimated that a small amount of product was formed, but the reaction was very slow. In other words, a homogeneous PST was not obtained under these conditions.

EXAMPLE 57

This example was an attempt to use aluminum oxide as the base. The reagents used were 365 g (0.4 moles) FHSO, 54.32 g of aluminum oxide, 5 g glacial acetic acid, and 0.5 g water. The reaction time was four hours and at a high temperature of 187° C. FTIRs were run at one hour and at the end of four hours. There was no evidence of reaction.

EXAMPLE 58

This example combined Zn(OH)$_2$ and Ca(OH)$_2$ in a 1:1 ratio by reacting 365 g (0.4 moles) FHSO, 19.87 g (0.2 moles) $Zn(OH)_2$, 14.81 g (0.2 moles) $Ca(OH)_2$, 5 g glacial acetic acid, and 0.5 g water. The reaction time was five hours and the temperature did not exceed 190° C. An FTIR was run several times during the reaction to observe any changes in the OH and carbonyl peaks. After two and one-half hours some of the correct peaks showed up but the OH peak was small. The reaction was continued to the end of five hours and another FTIR was run. This showed a small broad OH peak and an ester carbonyl peak that was larger than the metallic acid carbonyl peak. It appeared that the $Ca(OH)_2$ reacted as usual and the $Zn(OH)_2$ reacted very little.

EXAMPLE 59

This example was an attempt to use $Mg(OH)_2$ as the base by reacting 365 g (0.4 moles) FHSO, 23.33 g (0.4 moles) $Mg(OH)_2$, 5 g HOAc, and 0.5 g water. The reaction time was right at five hours and the reaction temperature did not exceed 190° C. FTIRs were run several times during the reaction and they showed no signs of reaction.

EXAMPLE 60

This example was another attempt to use Kadox 911 zinc oxide as the base by reacting 39 g (0.45 moles) FHSO, 36.76 g (0.45 moles) Kadox 911, 5 g glacial acetic acid, and 0.5 g water. The reaction time extended over nine hours and the reaction temperature got as high as 197° C. FTIRs run on the reaction mixture during this reaction time showed no significant change. In other words, a homogeneous PST was not obtained under these conditions.

EXAMPLE 61

In this example a different oil was used to help the solubility of the reagents and the reaction. The reagents used included 353.6 g (0.4 moles) SBO, 32.54 g (0.4 moles) Aldrich ZnO, 5 g glacial acetic acid, and 0.5 g water. The reaction started with a white suspension of the ZnO in the hot oil and at the end of the reaction undissolved solids were seen in the flask. The reaction time was about ten hours and twenty-five minutes and the temperature did not exceed 210° C. The FTIR was used to monitor the reaction and a change in the peak height of the metallic acid salt carbonyl function was observed. The height of the ester carbonyl peak got shorter and the metallic acid carbonyl peak got higher. This reaction was very slow but apparently some new material was produced. The HPLC of the reaction product showed some mono, di, and triglyceride peaks but it also showed a very strong peak at a retention time of 3.583 minutes that could not be identified. In other words, a homogeneous PST was not obtained under these conditions.

EXAMPLE 62

In this example, the reagents were reacted cold by blending 39.6 g Pationic® 919 (FHSO, powdered), 3.3 g $Ca(OH)_2$, 0.5 g HOAc, and 0.2 g water in a Waring blender for fifteen minutes. The resulting mixture was kept at room temperature for two weeks and then monitored with the FTIR. Examination of the resulting spectra showed no significant indications of reaction.

EXAMPLE 63

In this example, 2 g calcium acetate, 365 g FHSO (0.4 moles), and 29.63 g (0.4 moles) $Ca(OH)_2$ were reacted. The temperature rose to 176° C. This reaction did not go under these conditions. However, when 1 g glacial acetic acid and one half ml water were added, the reaction went as usual.

EXAMPLE 64

The kinetics of the reaction was studied by using 365 g (0.4 moles) FHSO, 29.63 g (0.4 moles) $Ca(OH)_2$, 2.5 g glacial acetic acid, and 0.5 g water. Six samples were taken at intervals during the reaction for FTIR curves. This information gave some insight into the development of the different products. HPLCs of the various fractions were also run. One can see the progressive development of the mono, di, and triglycerides.

EXAMPLE 65

The variable in this example was to use 1 g HOAc in the reaction with normal amounts of FHSO and $Ca(OH)_2$ and water. The reaction went as usual and the correct peaks appeared on the FTIR.

EXAMPLE 66

This example used anhydrous conditions to determine if water was really necessary by reacting 365 g (0.4 moles) FHSO, 29.63 g (0.4 moles) and 5 g glacial acetic acid. This reaction went about two hours and fifteen minutes, the temperature rose to 175° C. and samples run on the FTIR showed that the reaction went satisfactorily. There was, however, a bad odor from the product, probably from side reactions of the glycerine.

EXAMPLE 67

The variable in this example was temperature. The temperature was maintained as close to 150° C. as possible during reaction of 365 g (0.4 moles) FHSO, 29.63 g $Ca(OH)_2$, 5 g glacial acetic acid, and 0.5 g water. The reaction time was two hours and the temperature at the highest rose to 153° C. The reaction went as usual and the FTIR showed the correct peaks.

EXAMPLE 68

The variable in this example was to use 0.1 g glacial acetic acid to determine if this small amount would make the reaction go by using 365 g (0.4 moles) FHSO, 29.63 g $Ca(OH)_2$, 0.5 g water and 0.1 g glacial acetic acid. The reaction was run for three and one half hours at temperatures up to 190° C. The FTIR analysis after this time showed that no reaction had taken place.

EXAMPLE 69

The variable in this example was temperature. The reagents consisted of 365 g (0.4 moles) FHSO, 29.63 g (0.4 moles) $Ca(OH)_2$, 0.5 g water, and 5 g HOAc. The temperature was maintained around 120° C. for six hours. The FTIR showed that there was no reaction after six hours at this temperature. The next day this same reaction was heated to 178° C. and the reaction went to completion in about one hour. Temperature was definitely a controlling factor.

EXAMPLE 70

For comparative purposes, 187.5 g FHSO, 16.5 g $Ca(OH)_2$, and 15 g water were reacted. The reaction temperature remained around 100° C. for two hours and twenty minutes and the FTIR showed no reaction at this point. As an experiment, 2 g of NaOH were added, hoping to make enough soap to help the reaction go. The reaction was continued for another hour and the temperature rose to 190° C. The reaction now seemed to go as usual and the FTIR showed that the correct peaks were there but there also seemed to be a $Ca(OH)_2$ peak, but only to a small extent.

EXAMPLE 71

The variable in this example was to use an ester catalyst in the reaction and ethyl acetate was selected. The reagents were 365 g (0.4 moles) FHSO, 29.63 g (0.4 moles) Ca(OH)$_2$, 0.5 g water, and 10 g ethyl acetate. The reaction temperature rose to 178° C. for a period of two hours and the FTIR analysis showed no reaction.

EXAMPLE 72

The variable in this example was the use of erucamide as a catalyst. The reagents were 356 g (0.4 moles) FHSO, 29.64 g (0.4 moles) Ca(OH)$_2$, 0.5 g water, and 5.0 g erucamide. This reaction was run for three hours at temperatures up to 178° C. At the end of this time the FTIR showed a very small metallic acid carbonyl peak and no OH peak.

EXAMPLE 73

The variable in this example was diethanolamine. The reagents were 365 g (0.4 moles) FHSO, 29.63 g (0.4 moles) Ca(OH)$_2$, 0.5 g water, and 5.08 g diethanolamine. The reaction was run for a total of four hours at temperatures up to 183° C. At the end of this time an FTIR of the reaction mixture showed that the reaction went. The total mono adjusted was 16.04%, di=14.5%, tri=6.45%, % Ca ash= 4.01%, FG=1.98%, 1-mono=13.7%, FFA=0.46%, and the CMP=105–110° C.

EXAMPLE 74

The variable in this example was to use Pamolyn® 100 (90% oleic acid) as a catalyst by reacting 365 g (0.4 moles) FHSO, 29.63 g (0.4 moles) Ca(OH)$_2$, 0.5 g water, and 5.0g Pamolyn® 100. This reaction was run over a five-hour period with temperatures not over 181° C. The FTIR after this time looked good and the adjusted total mono=16.89%, di=16.81%, tri=7.72%, % Ca ash=6.98%, FG=1.78%, 1-mono=13.42%, FFA=0.76% and the m.p.=109–113° C.

EXAMPLE 75

Epoxidized soybean oil was used as the triglyceride in this example, by reacting 354 g (0.4 moles) epoxidized soybean oil, 29.63 g (0.4 moles) Ca(OH)$_2$, 5 g HOAc, and 0.5 g water. The reaction was run for two hours and at temperatures around 195° C. During this reaction a large hard ball formed in the flask and after one hour the lump disappeared. Something in this reaction initiated an exotherm and the temperature shot up to 215° C. The reaction mixture here was very dark and looked like decomposition material. The FTIR showed an OH peak, a very tall ester peak, and a very small metallic acid peak. It is felt that side reactions occurred with the epoxy groups.

EXAMPLE 76

This example used a 33 IV lard as the triglyceride by reacting 343 g (0.4 moles) 33 IV lard, 29.63 g (0.4 moles) Ca(OH)$_2$, 5 g HOAc, and 0.5 g water at temperatures no higher than 185° C. for one and one-half hours. The reaction went nicely and poured out clear. The FTIR looks good and the total mono on an adjusted basis was 18.01%, the di=16.57%, the tri=6.58%, the % ash=4.12%, FG=2.07%, 1-mono=14.32%, moisture=0.71%, FFA=1.40%, and the m.p.=107–109° C.

EXAMPLE 77

A 68 IV lard was used in this example by reacting 345 g (0.4 moles) 68 IV lard, 29.63 g (0.4 moles) Ca(OH)$_2$, 5 g HOAc, and 0.5 g water at temperatures no higher than 178° C. for one hour and ten minutes. This reaction proceeded as usual and an FTIR of the final material looked good. The final product was a thick amber liquid. The total mono on an adjusted basis=17.4%, di=14.16%, tri=6.57%, ash=4.12%, FG=2.28%, 1-mono=14.39%, moisture=1.12%, FFA= 1.89%, and the CMP=25–64° C. Also the HPLC on this product showed an extra strong peak that could not be identified.

EXAMPLE 78

This example reacted 345 g (0.4 moles) deodorized tallow, 29.63 g (0.4 moles) Ca(OH)$_2$, 5 g HOAc, and 0.5 g water at temperatures no higher than 180° C. for one hour and ten minutes. The reaction went as usual and the end product was a very light amber clear liquid. The FTIR showed the correct peaks and the HPLC showed an extra strong peak that could not be identified. The total corrected mono=18.09%, di=15.73%, tri=7.65%, FG=2.25, 1-mono= 14.14%, moisture=0.84%, FFA=2.03%, CMP=20–70° C.

EXAMPLE 79

This example was an attempt to prehydrolyze the fat and then add the Mg(OH)$_2$. Reagents were 365 g FHSO (0.4 moles), 5 HOAc, 0.2 g water and 23.32 g Mg(OH)$_2$. Reacted all the reagents except the Mg(OH)$_2$ for three hours at temperatures around 178° C. After this time an FTIR was taken and no peaks of free acid were found. The Mg(OH)$_2$ was now added and the reaction continued at temperatures up to 193° C. for five and one-half hours. An FTIR sample and showed no indication of reaction.

EXAMPLE 80

This example was an attempt to prehydrolyze the fat and then add the Zn(OH)$_2$. Reagents were 365 g (0.4 moles) FHSO, 5 g HOAc, 0.5 g water and 39.75 g Zn(OH)$_2$. The reaction mixture was heated without the Zn(OH)$_2$ for three hours at temperatures up to 185° C. A sample was then taken for an FTIR and there were no peaks of free acids observed. The Zn(OH)$_2$ was added and the reaction continued at temperatures up to 186° C. for nine and one-half more hours. A sample was taken for an FTIR and the results showed no hydroxyl peak and perhaps there was some metallic carbonyl peak. The material had a strong odor. In other words, a homogeneous PST was not obtained under these conditions.

EXAMPLE 81

The purpose of this example was to try to distill off any excess glycerine formed in the reaction. The reagents consisted of 365 g (0.4 moles) FHSO, 29.63 g Ca(OH)$_2$, 5.0 g HOAc, and 0.5 g water. The reaction was run for about one hour and thirty-five minutes and the temperature did not exceed 187° C. At the end of this time the nitrogen tube was removed and a vacuum applied to the flask in an attempt to remove the glycerine. The reaction mixture bubbled as in a normal distillation but no glycerine was observed in the condenser flask, perhaps because such a small amount of glycerine was removed. The analysis of this reaction mixture showed a glycerine of 1.00%. HPLC analysis showed mono=8.12%, di=17.66%, and the tri=13.14%. The 1-mono=9.11%, moisture=0.53%, FFA=0.5%, and the m.p.= 68–115° C.

EXAMPLE 82

This example used macadamia nut oil, the molecular weight figured at 840, by reacting 168 g (0.2 moles) of the oil, 14.81 g Ca(OH)$_2$, (0.2 moles), 2.5 g HOAc, and 0.5 g H$_2$O. This reaction was run for one and one half hours and the temperature did not rise above 184° C. At the end of this time an FTIR was taken and the required peaks were observed. The HPLC showed 17.23% mono, 17.87% di, and 8.76% triglyceride. A large unknown peak was observed on the HPLC. The Ca=4.26%, FG=1.73%, 1-mono=13.47%, moisture=0.24%, FFA=0.7%. The melting point was unable to be taken. The reaction product is a semi solid.

EXAMPLE 83

This example was an attempt to use triphenylphosphite as a catalyst in place of the glacial acetic acid by using 365.0 g FHSO (0.4 moles), 29.63 g (0.4 moles) Ca(OH)$_2$, 0.5 g water and 5.0 g triphenylphosphite. The reaction was run for four hours and the temperature did not rise above 183° C. At several times during the reaction an FTIR was run to see if the reaction was going but at no time were the correct peaks observed on the FTIR.

EXAMPLE 84

The variable in this example was tris (nonyl phenyl) phosphite as a catalyst by reacting 365.0 g (0.4 moles) FHSO, 29.63 g (0.4 moles) Ca(OH)$_2$, 5 g tris (nonyl phenyl) phosphite, and 0.5 g water was used. The reaction was run over four hours and the temperature did not rise above 187° C. An FTIR was taken at the end of the reaction and showed no signs that the reaction went.

EXAMPLE 85

Diethylamine was tried as a catalyst in this example by reacting 365.0 g (0.4 moles) FHSO, 29.63 g Ca(OH)$_2$ (0.4 moles), 5.0 g diethylamine, and 0.5 g water. The reaction was run for about 5 hours and the temperature did not rise above 185° C. An FTIR was run and the resulting spectra showed no signs that the reaction went.

EXAMPLE 86

Para-toluenesulfonic acid was tried as a catalyst in this example, by reacting the same amounts of reagents as in Example 85 with the exception that p-toluene sulfonic acid was used in place of the diethylamine. This reaction was run for over four hours and the temperature did not rise above 183° C. An FTIR was run and the resulting spectra showed no signs that the reaction went.

II. Partially Saponified Triglyerides as Polymer Additives
A. Lubricants for PVC Rigid PVC pipe usually contains a multi-component lubricant system: (a) a 165° F. melt paraffin wax, (b) calcium stearate, and (c) an oxidized, high molecular weight, polyethylene wax. Together, these components generally comprise 1.5 parts per hundred parts of resin (phr) in the formulation. They function in the rigid PVC compound during extrusion to increase its heat stability and to slow the melt-fusion process so the PVC resin will not prematurely fuse in the extruder.

Lubricants for PVC are considered "internal" or "external" based on their specific functionality in the polymer. Internal lubricants reduce melt viscosity and intra-polymer friction, and produce little effect on fusion time. External lubricants retard fusion and lubricate between the polymer and the processing equipment. For detailed information on rigid PVC lubricants see "The Lubrication Mechanism of Calcium Stearate/Paraffin Wax Systems in PVC Compounds", by Rabinovitch, Lacatus and Summers; presented at ANTEC '84.

In the examples that follow, the PST of each of the foregoing Examples 34, 40, 41, 51 and 46 were evaluated at 1.5 parts in the following formulation, and compared to an un-lubricated control.

| Material | Grade | phr | Source |
|---|---|---|---|
| PVC | Geon G27 | 100.0 | The Geon Company |
| CaCO$_3$ | Gammasperse CS-11 | 3.0 | Georgia Marble |
| TiO$_2$ | TITANOX 2071 | 1.0 | Kronos |
| Organotin mercaptide stabilizer | Advastab TM-694 | 0.4 | Carstab |

Testing was done in a Haake PolyLab© torque rheometer. Conditions were as follows: 70 g charge, rotor speed of 60 RPM, chamber at 180° C., with intermittent 30 psi air-cooling. All fixed formulation components were master-batched. Individual components were weighed to each charge prior to the test run. A three-minute "soak time" allowed the charge to warm up before starting the rotors. Heat stability and fusion times were averaged from three runs. The results are reported in Table 1A.

TABLE 1A

| Total Lubricant (1.5 phr) | PST Type | Fusion (seconds) | Stability (seconds) |
|---|---|---|---|
| None | n/a | 7 | 199 |
| Example 40 | Ca FHSO | 7 | 270 |
| Example 41 | Ca FHT | 7 | 234 |
| Example 51 | Ca PHSO | 7 | 280 |
| Example 34 | hi Ca FHSO | 5 | 249 |

Effective internal lubricants for rigid PVC can increase stability by lowering the frictional heat generated during processing. The addition of each calcium PST increased the stability of the rigid PVC test formulation.

The result for sodium PST is reported in Table 1B.

TABLE 1B

| Total Lubricant (1.5 phr) | PST Type | Fusion (seconds) | Stability (seconds) |
|---|---|---|---|
| None | n/a | 7 | 199 |
| Example 46 | Na FHSO | 60 | 150 |

Effective external lubricants for rigid PVC increase fusion time by lubricating the resin particles before melt-fusion occurs. This prevents premature fusion in the extruder barrel during processing. The addition of the sodium PST increased the fusion time of the rigid PVC test formulation.
B. Antistats for PVC PVC resin particles are prone to developing static electrical charges. This is primarily due to a powerful frictional effect. This triboelectricity manifests itself when the resin is conveyed from drying, to and from storage, to and from and during blending, and to melt processing. Resin particles will not properly flow or fill in such cases.

Additives are used to mitigate this static electrical buildup. Often agents such as polyhydroxy organic compounds are used. These compounds attract moisture, which dissipates the static charge. In other cases, a finely divided solid phase lubricant is used. Certain fine particulates can lubricate between PVC particles during conveyance and mixing, preventing the formation of static charges. We have found that PSTs are excellent lubricants for PVC resin particles, preventing static charge buildup, thereby facilitating flow and fill.

As a test for antistatic properties, the bulk density of PVC resin is typically measured after a static charge has been imparted to it. When charged, less PVC resin will occupy a given volume. The static charge is typically applied by mixing the resin, or resin plus additive, in a Hobart blender. The weight in grams needed to precisely fill a 100 ml cup is then measured. The higher the weight, the more successful the antistat protection.

The PSTs of each of the foregoing Examples 39, 40, 43, 45, 46 and 55 were tested for their antistatic properties, i.e., bulk densities, in PVC (Shintech SE-950EG). The procedure consisted of weighing 300 g PVC into a Hobart mixer, adding the PST of each Example as shown in Table 2, mixing for 15 minutes at #2 speed, and measuring bulk density per ASTM D 1895-69. The results in grams per 100 ml are reported in Table 2.

As a point of reference, untreated PVC will fill the 100 ml up with only 49.44 g after a static charge is imparted to it.

TABLE 2

| ppm | Density | ppm | Density |
|---|---|---|---|
| Example 40 (Ca FHSO) | | Example 39 (Ca FHP) | |
| 500 | 51.7 | 500 | 49.8 |
| 1000 | 55.6 | 1000 | 53.0 |
| 1500 | 56.4 | 1500 | 54.4 |
| 2000 | 57.2 | 2000 | 55.6 |
| 2500 | 57.9 | 2500 | 56.1 |
| Example 43 (Ca FHHER) | | Example 46 (Na FHSO) (1/89) | |
| 500 | 52.7 | 500 | 49.92 |
| 1000 | 54.8 | 1000 | 50.78 |
| 1500 | 56.1 | 1500 | 51.63 |
| 2000 | 56.9 | 2000 | 52.90 |
| 2500 | 57.4 | 2500 | 52.45 |
| Example 55 (Ca 12-OH) St | | Example 45 (K FHSO) (1/98) | |
| 500 | 46.7 | 500 | 51.99 |
| 1000 | 52.3 | 1000 | 52.96 |
| 1500 | 55.2 | 1500 | 53.67 |
| 2000 | 56.2 | 2000 | 54.22 |
| 2500 | 57.8 | 2500 | 54.31 |

At 1000, 1500, 2000 and 2500 ppm, every PST demonstrated significant bulk density improvements over the untreated resin. Even at 500 ppm, the very lowest additive level, the PSTs of Examples 40, 43 and 45 showed significant effectiveness.

C. Neutralizers for Polyolefins

Polyolefins made using acidic catalysts (e.g., Ziegler-Natta) contain acidic catalyst residues. These require neutralization to prevent corrosion of processing equipment and adverse interactions with other additives. These polyolefins include most polypropylenes, and linear low density and high-density polyethylenes. Other polymers develop acidity through their own degradation (such as EVA or PVC) or the decomposition of potentially acidic additives such as phosphites or halogenated flame retardants.

Neutralizers for these resins are usually selected from a group of soluble or dispersible bases which react with acidic catalyst residues. Typically, these additives are metallic stearates, dispersible inorganics, or specialty products based on lactic acid chemistry. They are more completely described by D. Dieckmann in his paper entitled "Lactic Acid Derivatives As Neutralizers in Polypropylene" presented at the "Polyolefins VIII" Society of Plastics Engineers Regional Technical Conference on Feb. 22, 1993.

A drawback common to many neutralizers is an unfortunate tendency to plug extruder screens. Inorganic neutralizers, which are insoluble in the polymer, can plug extruder screens if their particle size is too large. Calcium stearate often has insoluble residuals that, unless carefully and expensively removed, can plug extruder screens.

It has been found that PSTs are highly effective neutralizers and, because they are soluble and homogeneous, PSTs do not tend to plug extruder screens.

The PST's of Examples 41, 40, 34, 44, 46, 48 and 51 were tested as neutralizers for polyolefin resins, namely, polypropylene (PP) and propylene-ethylene copolymer. The following formulations were Henschel mixed and extruded on the Killion 1" extruder with the following settings: 220° C., 120 rpms, 40/60/40-mesh screen pack. The formulations were then pelletized. Corrosion testing was performed per standard Patco procedure entitled "Test Method Polymer Corrosivity", Revised May 1, 1997, Supersedes Mar. 21, 1997, by Patco® Polymer Additives Division American Ingredients Company. The results are reported in Tables 3 and 4.

| PP Formulation | | |
|---|---|---|
| ProFax 6501 PP resin* | | (Montell Polyolefins) |
| Irganox 1010** | 500 ppm | (Ciba Additives) |
| Irgafos 168*** | 500 ppm | (Ciba Additives) |
| Neutralizer | 500 ppm | (PSTs, shown below) |

*polypropylene homopolymer
**tetrakis [methylene (3,5-di-t-butyl-4-hydroxyhydrocinnamate)]
***tri(2,4-di-t-butylphenyl) phosphite

TABLE 3

| | % Coverage | Severity |
|---|---|---|
| Example 41 (Ca FHT) | 0 | None |
| Example 40 (Ca FHSO) | 0 | None |
| Example 34 (Hi Ca) | 0 | None |
| Example 44 (Lo Ca) | 0 | None |
| Example 46 (Na FHSO) | 0 | None |
| Example 48 (Ca SBO) | 100 | Light |
| Example 51 (Ca PHSO) | 0 | None |
| No Neutralizer | 100 | Severe |
| PP Formulation | | |
| ProFax 7501 PP resin (propylene-ethylene copolymer) | | (Montell Polyolefins) |
| Irganox 1010 | 500 ppm | (Ciba Additives) |
| Irgafos 168 | 500 ppm | (Ciba Additives) |
| Neutralizer | 500 ppm | (PSTs, shown below) |

TABLE 4

| | % Coverage | Severity |
|---|---|---|
| Example 41 (Ca FHT) | 0 | None |
| Example 40 (Ca FHSO) | 0 | None |
| Example 34 (Hi Ca) | 0 | None |
| Example 44 (Lo Ca) | 0 | None |
| Example 46 (Na FHSO) | 0 | None |
| Example 48 (Ca SBO) | 0 | None |
| Example 51 (Ca PHSO) | 0 | None |
| No Neutralizer | 100 | Moderate |

The PSTs were demonstrated to be effective neutralizers for polyolefins with reference to Tables 3 and 4.

D. Other Polymer Additive Uses

The above detailed description and examples demonstrate the uses of PSTs as lubricants, antistats and neutralizers for polymers. In addition, the PSTs also function in other thermoplastic and thermosetting polymer compositions as stabilizers, coupling agents, waterproofing agents, viscosity controllers, surfactants, and thickening agents. When employed in the polymer composition for any of these purposes, the PST is generally used in an amount up to about 10% by weight of the polymer, more normally up to about 5%, and, especially, from about 0.05 to about 2% by weight of the polymer. The following Table 5 is a brief list of polymers additive end-uses for the PSTs.

TABLE 5

| Polymer | End-Use or Function |
| --- | --- |
| Acrylonitrite-butadiene-styrene (ABS) | process lube, mold release |
| Styrene-butadiene copolymers | process lube, mold release |
| Elastomers (thermoplastic or thermosetting) | anti-block or lubricant |
| Epoxides | mold release |
| Polyethylene vinylacetate (EVA) | lubricant or process aid |
| Polyesters (thermoplastic or thermosetting) | mold release, viscosity control |
| Melamine-formaldehyde | mold release |
| Diallyl phthalates | mold release |
| Nylons | anti-block, mold release |
| Polycarbonate (PC) | mold release |
| Polyethylene (PE) | acid neutralizer, mold release |
| Alkyds | process lube, mold release |
| Phenolics | process lube, mold release |
| Plastisols | viscosity control |
| Polypropylene (PP) | acid neutralizer, mold release |
| Polyvinylchloride (PVC) | stabilizer, lubricant, neutralizer |
| Urea-formaldehyde | mold release |
| Polyurethane | mold release |

Thus, it will be understood to a person of ordinary skill in light of the above description of thermoplastic and thermosetting polymers that the PSTs of this invention may be used in a wide variety of polymer compositions for a diversity of end-uses.

E. Other Areas of Use

In addition, the PSTs can be used in other areas, such as, a general lubricant, coupling agent, waterproofing agent, viscosity controller, surfactant and thickener. The following Table 6 is a brief list other areas of end-use and is not intended to be limiting.

TABLE 6

| Product/Process | End-Use or Function |
| --- | --- |
| Lubrication: | |
| Adhesives | release from backing paper, mold release, antiblock |
| Animal feed | powder flow aid, pellet mold release |
| Cement, concrete, stucco, mortar | mold release for cementitious parts, powder flow aid |
| Ceramics | mold release of "green" part, flow aid for ceramic powder |
| Sanding sealer | sanding lube |
| Powdered metal | mold release of "green" part, flow aid for metal powder |
| Rubber | antiblock, additive and pigment dispersant, mold release |
| Textile | antiblock, fiber process lube |
| Cosmetic powders | powder flow aid, skin soother |
| Cosmetic powders, compressed | ejection lube, compression lube, powder flow aid |
| Crayons | glide lube |
| Electrostatic toner | metal release |
| Fire extinguisher chemicals | powder flow aid |
| Metal drawing | die lubricant |
| Metal extrusion | die lubricant |

TABLE 6-continued

| Product/Process | End-Use or Function |
| --- | --- |
| Metal stamping | mold lubricant |
| Golf balls | rubber detackifier (center core) |
| Grinding wheels | mold release, grinding lubricant |
| Sandpaper | sanding lube |
| Ink | anti-tack (during and after drying) |
| Metal rolling | contact lubricant |
| Food tablets | compression lube, ejection lube |
| Instant lottery tickets | paper release (during scratch-off) |
| Food | anti-caking and flow aid |
| Paper coating | lubricates paper surface |
| Pencils | glide lube while writing |
| Pharmaceutical powders | flow aid |
| Pharmaceutical tablets | compression lube, ejection lube |
| Pigments | grinding aid-lubricates |
| Waterproofing: | |
| Commercial waterproofing | treating canvas, wood, masonry, etc. |
| Cement, concrete, stucco, mortar | water repellence, drying rate control |
| Cosmetic powders | water repellence |
| Explosives, pyrotechnics | water repellence |
| Fire extinguisher | water repellence |
| Ink | water repellence |
| Grease | water repellence |
| Paper coating | water repellence |
| Thickening: | |
| Paint | viscosity control, suspend pigments |
| Cosmetic creams | viscosity control, suspend solids |
| Ink | viscosity control, suspend pigments |
| Grease | viscosity control |
| Pharmaceutical gels | viscosity control |
| Pharmaceutical creams | viscosity control, suspend solids |
| Surfactant: | |
| Paint | pigment suspension |
| Rubber | disperse pigments, additives |
| Cosmetic powders | skin adhesion |
| Cosmetic creams | emulsifier |
| Defoamers | coupler, active surfactant |
| Grease | metal adhesion |
| Food | binder, emulsifier |
| Pigments | grinding aid-deagglomerates particles |
| Pharmaceutical creams | emulsifier |
| Appearance: | |
| Paint | flatting |
| Varnish & laquer | flatting |
| Shampoo | pearlizer, opacifier |
| Paper coating | gloss control |
| Miscellaneous: | |
| Catalyst | metal carrier |
| Crayons | hardener |
| Food | defoamer, stabilizer |

With reference to Table 6, the PST can be used in a product or process to provide lubrication, for example, as a lube for the powders, other particulates, and solid surfaces described. In almost all end-uses for the products or processes listed in Table 6, the PST can provide a lubricating function. However, the PST can also be used as a waterproofer for cement, concrete, cosmetic powders, explosives, pyrotechnics, inks, wood, etc. In the cases of paints, creams, defoamers, greases, etc., the PST can function as a coupling agent or thickener. The amount of the PST used for the particular purpose will vary and, as stated above, when used internally in a composition, up to about 10% by weight may be used. Otherwise, when the PST serves as an external lube for metal forming, grinding, etc., an effective amount is employed.

In view of the above detailed description, operating examples and comparative examples, the principles and best modes of this invention will be understood. However, other embodiments and equivalents of the invention may be derived therefrom and it is to be understood that they are within the scope of the invention.

What is claimed is:

1. A polymer composition comprising
   (a) a polymer selected from the group consisting of a thermoplastic polymer and a thermosetting polymer, and
   (b) an amount up to about 10% by weight of said polymer of a homogeneous partially saponified triglyceride (PST) composition having components consisting essentially of
      about 5 to about 95 percent by weight of a metal salt of a fatty acid of said triglyceride, and
      about 95 to about 5 percent by weight of a mixture of monoglyceride, diglyceride and triglyceride derived from said triglyceride, said homogeneous composition achieved in the absence of a compatibilizing agent for said components.

2. The polymer composition of claim 1 wherein said metal salt is selected from the group consisting of alkali and alkaline earth metal salts.

3. The polymer composition of claim 1 wherein said metal of said salt is selected from the group consisting of calcium, sodium, potassium and lithium, and mixtures thereof.

4. The polymer composition of claim 1 wherein said triglyceride is a natural fat or oil.

5. The polymer composition of claim 1 wherein said PST is derived from tallow, fully hydrogenated tallow, soybean oil, partially hydrolyzed soybean oil, fully hydrogenated soybean oil, fully hydrogenated high erucic rapeseed oil, fully hydrogenated castor oil, fully hydrogenated palm oil, canola oil, coconut oil, fully hydrogenated coconut oil, sunflower oil, lard, partially hydrogenated lard or macadamia oil.

6. The polymer composition of claim 1 wherein said metal salt is a calcium salt or sodium salt.

7. The polymer composition of claim 1 wherein said metal salt is contained in an amount of from about 75 to about 35 percent by weight and said glyceride mixture is contained in an amount of from about 25 to about 65 percent by weight.

8. The polymer composition of claim 1 wherein said PST composition is in an amount of up to about 5% by weight.

9. The polymer composition of claim 1 wherein said PST composition is in an amount of about 0.05 to about 2% by weight.

10. A polymer composition comprising
    (a) a polymer selected from the group consisting of a thermoplastic polymer and a thermosetting polymer, and
    (b) an effective amount of a homogeneous partially saponified triglyceride (PST) composition as an additive selected from the group consisting of an antistat, lubricant, stabilizer, coupling agent, waterproofing agent, and neutralizer for said polymer, said homogeneous composition having components consisting essentially of
       about 5 to about 95 percent by weight of a metal salt of a fatty acid of said triglyceride selected from the group consisting of alkali and alkaline earth metal salts, and
       about 95 to about 5 percent by weight of a mixture of monoglyceride, diglyceride and triglyceride derived from said triglyceride, said homogeneous composition achieved in the absence of a compatibilizing agent for said components.

11. The composition of claim 10 wherein said PST composition is in an amount up to about 5% by weight of said polymer.

12. The composition of claim 10 wherein said metal of said salt is selected from the group consisting of calcium, sodium, potassium and lithium, and mixtures thereof.

13. The composition of claim 12 wherein the PST composition is derived from tallow, fully hydrogenated tallow, soybean oil, partially hydrolyzed soybean oil, fully hydrogenated soybean oil, fully hydrogenated high erucic rapeseed oil, fully hydrogenated castor oil, fully hydrogenated palm oil, canola oil, coconut oil, fully hydrogenated coconut oil, sunflower oil, lard, partially hydrogenated lard or macadamia oil.

14. The composition of claim 13 wherein said thermoplastic polymer is selected from the group consisting of polyvinyl chloride, polyethylene vinyl acetate, polycarbonate, polyethylene, polypropylene, nylon, polystyrene-butadiene, polystyrene, acrylic resins, polyesters and elastomers.

15. The composition of claim 14 wherein said thermosetting polymer is selected from the group consisting of phenolics, alkyds, polyesters, epoxies, polyurethanes, diallyl phthalates, urea-formaldehydes, elastomers, and melamine-formaldehydes.

16. The composition of claim 14 wherein the PST composition is in an amount of about 0.05 to about 2% by weight of said polymer.

17. A homogeneous partially saponified triglyceride composition suitable for use as any one of the uses selected from the group consisting of a lubricant, coupling agent, viscosity controller, thickening agent, surfactant or water proofing agent having components consisting essentially of
    about 5 to about 95 percent by weight of a metal salt of a fatty acid of said triglyceride, and
    about 95 to about 5 percent by weight of a mixture of monoglyceride, diglyceride and triglyceride derived from said triglyceride, said homogeneous composition achieved in the absence of a compatibilizing agent for said components.

18. The composition of claim 17 wherein said metal salt is selected from the group consisting of alkali and alkaline earth metal salts.

19. The composition of claim 17 wherein said metal is selected from the group consisting of calcium, sodium, potassium and lithium, and mixtures thereof.

20. The composition of claim 17 wherein said triglyceride is a natural fat or oil.

21. The composition of claim 17 wherein the partially saponified triglyceride is derived from tallow, fully hydrogenated tallow, soybean oil, partially hydrolyzed soybean oil, fully hydrogenated soybean oil, fully hydrogenated high erucic rapeseed oil, fully hydrogenated castor oil, fully hydrogenated palm oil, canola oil, coconut oil, fully hydrogenated coconut oil, sunflower oil, lard, partially hydrogenated lard or macadamia oil.

22. The composition of claim 17 wherein said metal salt is a calcium salt or sodium salt.

23. The composition of claim 17 wherein said metal salt is contained in an amount of from about 75 to about 35 percent by weight and said glyceride mixture is contained in an amount of from about 25 to about 65 percent by weight.

* * * * *